(12) United States Patent
Xu et al.

(10) Patent No.: US 12,339,260 B2
(45) Date of Patent: Jun. 24, 2025

(54) METABONOMICS-BASED TOBACCO LEAF MILDEWING IDENTIFICATION METHOD

(71) Applicant: HONGYUNHONGHE TOBACCO (GROUP) CO., LTD, Yunan (CN)

(72) Inventors: Yueming Xu, Kunming (CN); Bin Chen, Kunming (CN); Jilai Zhou, Kunming (CN); Haiying Fang, Kunming (CN); Renjie Xu, Kunming (CN); Wenjing Yang, Kunming (CN); Zheng Mo, Kunming (CN); Peng Zhou, Kunming (CN)

(73) Assignee: HONGYUNHONGHE TOBACCO (GROUP) CO., LTD, Yunan (CN)

( * ) Notice: Subject to any disclaimer, the term of this patent is extended or adjusted under 35 U.S.C. 154(b) by 244 days.

(21) Appl. No.: 18/192,444

(22) Filed: Mar. 29, 2023

(65) Prior Publication Data
US 2023/0393106 A1 Dec. 7, 2023

(30) Foreign Application Priority Data
May 26, 2022 (CN) .......................... 202210590045.3

(51) Int. Cl.
*G01N 30/72* (2006.01)
*G01N 30/14* (2006.01)
*G01N 30/86* (2006.01)

(52) U.S. Cl.
CPC ......... *G01N 30/7206* (2013.01); *G01N 30/14* (2013.01); *G01N 30/86* (2013.01); *G01N 2333/37* (2013.01); *G01N 2333/415* (2013.01)

(58) Field of Classification Search
None
See application file for complete search history.

(56) References Cited

FOREIGN PATENT DOCUMENTS

| CN | 104820052 A | * | 8/2015 | |
|----|-------------|---|--------|---|
| CN | 109668992 A | * | 4/2019 | ............. G01N 30/86 |
| CN | 110346445 A | * | 10/2019 | ............. G01N 1/286 |

OTHER PUBLICATIONS

Zhang Chen et. al. (Editors), Guidelines for Quality Control of PCR Instruments; CIP Data in Books; Beijing Machinery Industry Press, 2021; 5ISBN978-7-111-67791-820, 1st Edition, 1st printing, May 2021.

(Continued)

*Primary Examiner* — Daniel S Larkin
(74) *Attorney, Agent, or Firm* — Sinorica International Patent & Trademark (57) ABSTRACT

A metabonomics-based tobacco leaf mildewing identification method, which comprises: obtaining tobacco leaf samples of the same variety, and carrying out artificial mildewing on a certain amount of tobacco leaf samples to obtain mildewed tobacco leaves; measuring volatile and semi-volatile components in the tobacco leaves before and after the tobacco leaf samples are mildewed by adopting a solid phase microextraction-gas chromatography-mass spectrometry method; performing data processing on the collected mass spectrum data to obtain the proportion content of different types of compounds in the mildewed sample and the normal sample, and further obtaining the change difference of the content of volatile compounds in the tobacco leaf sample before and after mildewing; and establishing a tobacco leaf mildewing identification model according to the discrimination variables.

10 Claims, 3 Drawing Sheets

(56) References Cited

OTHER PUBLICATIONS

Wang Jing et. al.; Research on Water Environment Characteristics and Water Quality Prediction Models and Algorithms in Water Source Areas—A Case Study of Qinhuangdao Region; Qinhuangdao: Yanshan University Press, May 2020; ISBN978-7-81142-176-7, Version: May 2020 First Edition Print: May 2020 First Printing.
Yang Lei; Effect of Environmental Factors on Quality of Tobacco Leaves and prediction method of mildew; Chinese Doctoral Dissertation; Kunming University of Science and Technology; Jan. 15, 2017; China.
Chen Sen-Lin et al.; Liquid Chromatography Coupled with Multivariate Statistics for Investigation of Relationship between Polyphenols and Aroma Types of Tobacco; Chinese Journal of Analytical Chemistry; vol. 47 Edition 5; May 2019; pp. 725-730; DOI: 10.19756 /j.issn. 0253-3820. 181680.

* cited by examiner

```
                                                           ┌─ S1
┌─────────────────────────────────────────────────────────┐
│ obtaining tobacco leaf samples of the same variety, and │
│ carrying out artificial mildewing on a certain amount   │
│ of tobacco leaf samples to obtain mildewed tobacco      │
│ leaves to obtain normal samples and mildewed samples    │
└─────────────────────────────────────────────────────────┘
                            │
                                                           ┌─ S2
┌─────────────────────────────────────────────────────────┐
│ measuring volatile and semi-volatile components in the  │
│ tobacco leaves before and after the tobacco leaf samples│
│ are mildewed by adopting a solid phase microextraction- │
│ gas chromatography-mass spectrometry method to obtain   │
│ mass spectrometry data                                  │
└─────────────────────────────────────────────────────────┘
                            │
                                                           ┌─ S3
┌─────────────────────────────────────────────────────────┐
│ performing data processing on the collected mass        │
│ spectrum data to obtain the proportion content of       │
│ different types of compounds in the mildewed sample     │
│ and the normal sample,and further obtaining the change  │
│ difference of the content of volatile compounds in the  │
│ tobacco leaf sample before and after mildewing to screen│
│ out a discrimination variable of the mildewed tobacco   │
│ leaf                                                    │
└─────────────────────────────────────────────────────────┘
                            │
                                                           ┌─ S4
┌─────────────────────────────────────────────────────────┐
│ establishing a tobacco leaf mildewing identification    │
│ model according to the discrimination variables, and    │
│ performing mildewing identification on the tobacco      │
│ leaves through the identification model                 │
└─────────────────────────────────────────────────────────┘
```

METABONOMICS-BASED TOBACCO LEAF MILDEWING IDENTIFICATION METHOD

TECHNICAL FIELD

The present invention relates to the technical field of tobacco leaf detection, and in particular, to a metabonomics-based tobacco leaf mildewing identification method.

BACKGROUND ART

As agricultural products, tobacco leaves are easily affected by environmental factors in the growth, storage, and alcoholization process, resulting in serious economic losses in cigarette enterprises. Mildewed tobacco leaves not only affect the appearance and quality of tobacco leaves but also produce toxic metabolites (such as aflatoxin) and attached pathogenic microorganisms, which can cause potential hazards to the health of smokers.

In recent years, the research on mildew tobacco has been paid more and more attention by tobacco enterprises, tobacco researchers, and the State Tobacco Monopoly Administration (STMA). The identification of mildew tobacco has become one of the key issues to be urgently solved for tobacco quality evaluation and flavor enhancement. At present, the prevention of tobacco mildew mainly depends on manual intervention, which consumes a lot of manpower and financial resources but is difficult to solve the key problems, such as the mechanism and reasons for mildew. The existing mechanism of tobacco leaf mildew and anti-mildew technology mainly include the effects of environmental conditions such as nutrients and bacteria, temperature and humidity on tobacco leaf mildewing, while there are few studies on the metabolism of tobacco leaf mildewing process. Therefore, how identifying tobacco leaf mildewing to improve tobacco quality has important significance.

SUMMARY OF THE INVENTION

The present invention provides a metabonomics-based tobacco leaf mildewing identification method, which solves the problems of inaccuracy and low efficiency in the existing tobacco leaf mildewing identification. The accuracy and efficiency of tobacco mildew identification can be improved, the quality of tobacco shreds is improved, and health hazards to smokers are reduced.

To achieve the above purposes, the present invention provides the following technical solutions:

A metabonomics-based tobacco leaf mildewing identification method, comprising: obtaining tobacco leaf samples of the same variety, and carrying out artificial mildewing on a certain amount of tobacco leaf samples to obtain mildewed tobacco leaves to obtain normal samples and mildewed samples;

measuring volatile and semi-volatile components in the tobacco leaves before and after the tobacco leaf samples are mildewed by adopting a solid phase micro-extraction-gas chromatography-mass spectrometry (SPME-GC-MS) method to obtain mass spectrometry data;

performing data processing on the collected mass spectrum data to obtain the proportion content of different types of compounds in the mildewed sample and the normal sample, and further obtaining the change difference of the content of volatile compounds in the tobacco leaf sample before and after mildewing to screen out a discrimination variable of the mildewed tobacco leaf, and establishing a tobacco leaf mildewing identification model according to the discrimination variables, and performing mildewing identification on the tobacco leaves through the identification model.

Preferably, the performing data processing on the collected mass spectrum data, comprises: plotting a volcano map by mass spectrometry data, and analyzing the content of volatile compounds in tobacco samples before and after mildewing by the volcano map.

Preferably, the performing data processing on the collected mass spectrum data further comprises:

analyzing the changes of volatile compounds in tobacco samples before and after mildewing by principal component analysis (PCA).

Preferably, the performing data processing on the collected mass spectrum data further comprises:

calculating the difference of chemical components in tobacco samples before and after mildewing by using the orthogonal partial least squares method, to determine the contribution value of various chemical components to tobacco leaf mildewing, and then determining the discriminant variable according to the contribution value.

Preferably, the performing data processing on the collected mass spectrum data further comprises:

analyzing changes of volatile compounds in tobacco samples before and after mildewing directly by visual analysis using thermal map analysis and hierarchical cluster analysis.

Preferably, the obtaining the proportion content of different kinds of compounds in the mildewed sample and the normal sample comprises:

identifying the mass spectrometry data by searching the NIST standard spectrum library, and calculating the relative content of each substance by peak area normalization method, to obtain the proportion result of different compounds in the mildewed sample and the normal sample, and performing data standardization and normalization processing on the collected proportion result of volatile compounds to obtain the difference of volatile compounds content in tobacco samples before and after mildewing.

Preferably, carrying out artificial mildewing on a certain amount of tobacco leaf samples, comprising:

adjusting the moisture content of the tobacco leaves of the tobacco leaf samples to make the moisture content of tobacco leaf above 18%, the moisture content of the tobacco leaf being determined by using an oven drying method;

placing the pretreated tobacco leaf sample into a constant temperature and humidity box, and adjusting the temperature and relative humidity to be 28° C. and 70%, respectively, to perform a tobacco leaf mildewing test.

Preferably, the sampling temperature of the tobacco leaf sample during the micro-extraction is 280° C. and the desorption lasts for 2 min.

Preferably, the gas chromatography conditions are as follows: injection port temperature: 280° C.; carrier gas: He; flow rate: 1 mL/min; heating conditions: initial temperature: 50° C., holding for 2 min, rising to 140° C. at 5° C./min and holding for 1 min, then rising to 280° C. at 10° C./min and holding for 1 min.

Preferably, establishing a tobacco leaf mildewing identification model according to the discrimination variables comprises:

performing Fisher stepwise discriminant analysis on volatile compounds in tobacco samples to screen out the discriminant variables effective for discriminating mildew tobacco, and establishing a Fisher linear discriminant function according to the discriminant variables.

The present invention provides a metabonomics-based tobacco leaf mildewing identification method, which determines the volatile and semi-volatile components in tobacco leaves before and after mildewing by using solid phase microextraction-gas chromatography-mass spectrometry, analyzes the differences of metabolites before and after mildewing by using non-targeted metabonomics combined with multivariate statistical analysis and constructs a prediction model to identify the quality of mildewed tobacco leaves, and predicts and monitors mildewed tobacco leaves in advance and in real-time. The accuracy and efficiency of tobacco mildew identification can be improved, the quality of tobacco shreds is improved, and health hazards to smokers are reduced.

BRIEF DESCRIPTION OF THE DRAWINGS

To more clearly explain the specific embodiments of the present invention, the following will give a brief introduction to the drawings needed in the embodiments.

DETAILED DESCRIPTION OF THE INVENTION

To enable those in the art to better understand the scheme of the embodiments of the present invention, the embodiments of the present invention will be further described in detail with the accompanying drawings and implementations.

Because of the problems of low efficiency and inaccuracy in current tobacco leaf mildewing identification, the present invention provides a metabonomics-based tobacco leaf mildewing identification method, which solves the problems of inaccuracy and low efficiency of the existing tobacco leaf mildewing identification. The accuracy and efficiency of tobacco mildew identification can be improved, the quality of tobacco shreds is improved, and health hazards to smokers are reduced.

Figure 1:
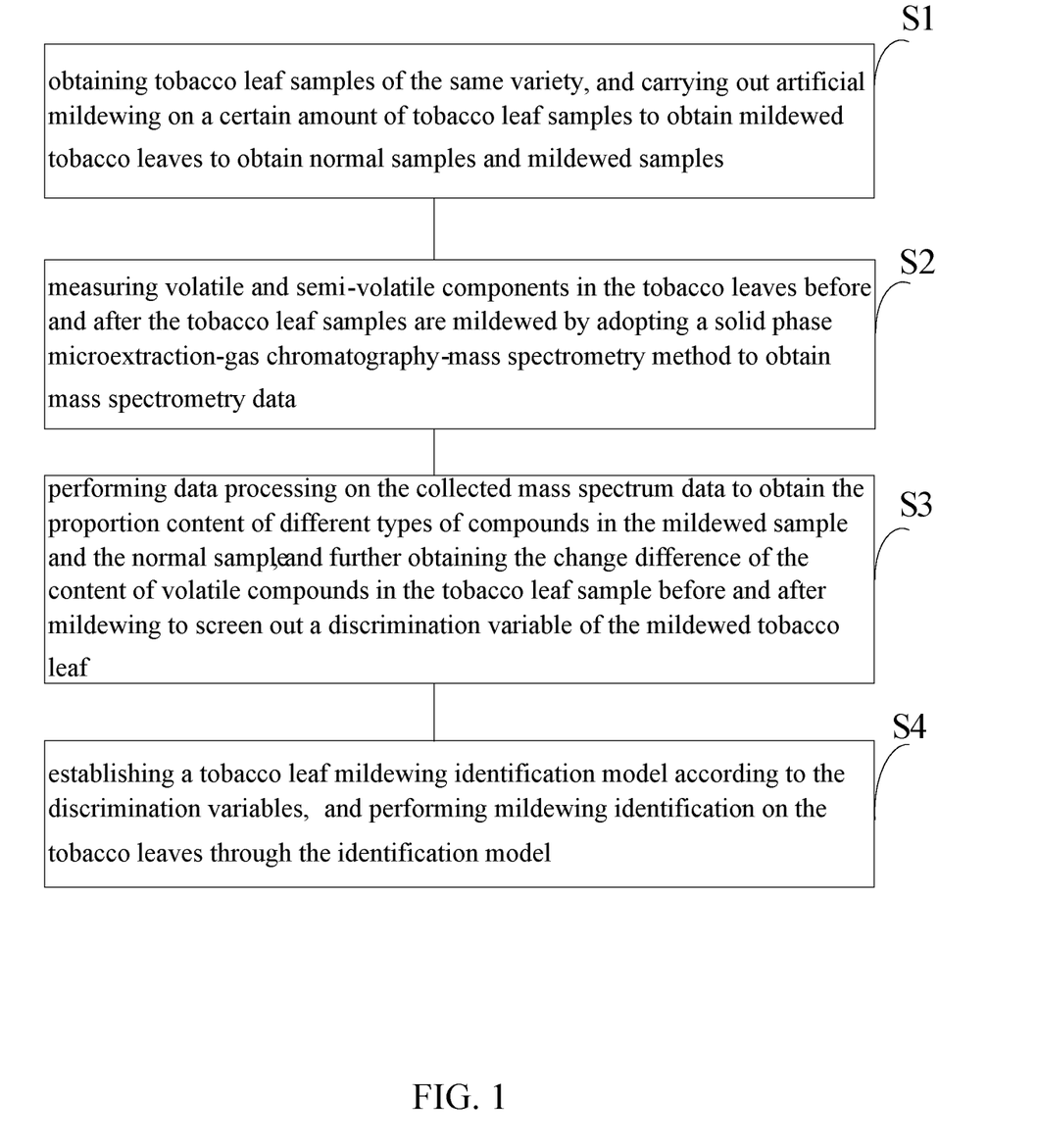
FIG. 1 is a schematic diagram of a metabonomics-based tobacco leaf mildewing identification method provided by the present invention.
Figure 2:
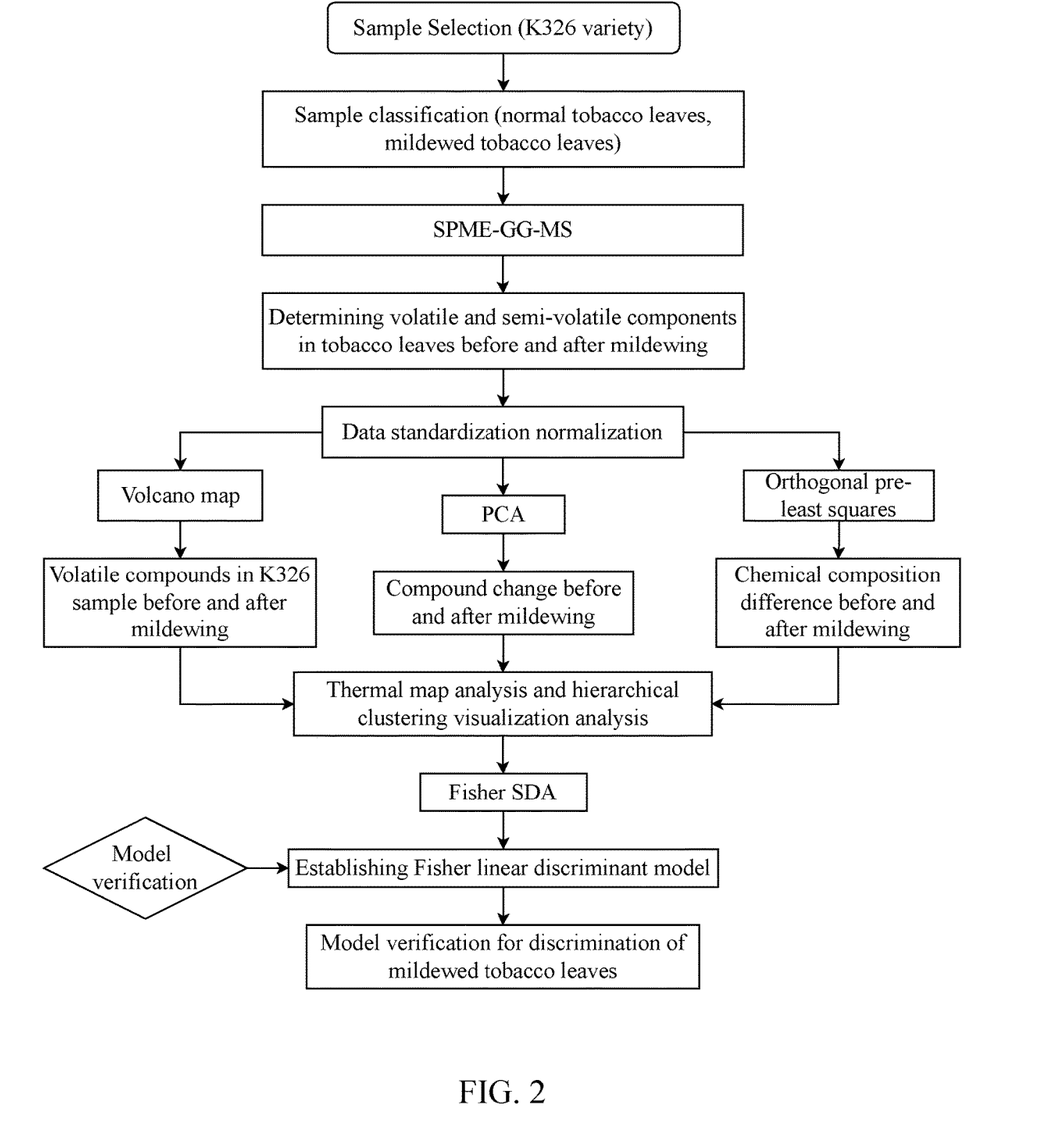
FIG. 2 is a flow chart of tobacco leaf mildewing identification provided by the present invention.

As shown in FIGS. 1 and 2, a metabonomics-based tobacco leaf mildewing identification method, comprises:

S1: obtaining tobacco leaf samples of the same variety, and carrying out artificial mildewing on a certain amount of tobacco leaf samples to obtain mildewed tobacco leaves to obtain normal samples and mildewed samples.

S2: measuring volatile and semi-volatile components in the tobacco leaves before and after the tobacco leaf samples are mildewed by adopting a solid phase microextraction-gas chromatography-mass spectrometry method to obtain mass spectrometry data.

S3: performing data processing on the collected mass spectrum data to obtain the proportion content of different types of compounds in the mildewed sample and the normal sample, and further obtaining the change difference of the content of volatile compounds in the tobacco leaf sample before and after mildewing to screen out a discrimination variable of the mildewed tobacco leaf.

S4: establishing a tobacco leaf mildewing identification model according to the discrimination variables, and performing mildewing identification on the tobacco leaves through the identification model.

Specifically, in an embodiment, the following steps were included:

Step 1: the stored tobacco leaves of K326 variety were subjected to artificial mildewing, and the tobacco samples were divided into normal tobacco leaves and mildewed tobacco leaves.

The moisture content of the tobacco leaves of the tobacco leaf samples was adjusted to make the moisture content of the tobacco leaf above 18%. The moisture content of the tobacco leaf was determined by using an oven-drying method. The pretreated samples of stored tobacco leaves were placed into a constant temperature and humidity box. The temperature and relative humidity were adjusted to be 28° C. and 70%, respectively, to perform a tobacco leaf mildewing test, with 30 days as the experimental period. The mildewed tobacco leaves were removed from the constant temperature and humidity box and stored in a −18° C. freezer for later use. Information table data of the stored tobacco samples are shown in Table 1.

TABLE 1

Information Table of Stored Tobacco Samples

| No. | Year | Variety | Grade | Origin |
|---|---|---|---|---|
| 1 | 2017 | K326 | WDC4Q | Baoshan, Yunnan |
| 2 | 2017 | K326 | WDC3F | Kunming, Yunnan |
| 3 | 2018 | K326 | WDX2F | Kunming, Yunnan |
| 4 | 2018 | K326 | WDX2F | Kunming, Yunnan |
| 5 | 2018 | K326 | WBBSF | Kunming, Yunnan |
| 6 | 2018 | K326 | WBBSF | Kunming, Yunnan |
| 7 | 2018 | K326 | WDB3F | Kunming, Yunnan |
| 8 | 2018 | K326 | WDC4F | Kunming, Yunnan |
| 9 | 2018 | K326 | WDC3F | Kunming, Yunnan |
| 10 | 2019 | K326 | WBBSF | Kunming, Yunnan |
| 11 | 2019 | K326 | WBBSF | Kunming, Yunnan |
| 12 | 2019 | K326 | WBBSQ | Tengchong, Yunnan |
| 13 | 2019 | K326 | WDC4F | Kunming, Yunnan |
| 14 | 2019 | K326 | WDC3F | Kunming, Yunnan |
| 15 | 2019 | K326 | WCCSF | Kunming, Yunnan |
| 16 | 2020 | K326 | WCCSF | Kunming, Yunnan |
| 17 | 2020 | K326 | WDC3F | Kunming, Yunnan |
| 18 | 2020 | K326 | WCCSF | Kunming, Yunnan |
| 19 | 2020 | K326 | WCCSF | Kunming, Yunnan |
| 20 | 2020 | K326 | WCCSF | Kunming, Yunnan |
| 21 | 2020 | K326 | WCCSF | Kunming, Yunnan |

TABLE 1-continued

Information Table of Stored Tobacco Samples

| No. | Year | Variety | Grade | Origin |
|---|---|---|---|---|
| 22 | 2020 | K326 | WCCSF | Kunming, Yunnan |
| 23 | 2020 | K326 | WCCSF | Kunming, Yunnan |
| 24 | 2020 | K326 | WDC3F | Kunming, Yunnan |
| 25 | 2020 | K326 | WDC3F | Kunming, Yunnan |
| 26 | 2020 | K326 | WDC3F | Kunming, Yunnan |
| 27 | 2020 | K326 | WBBSF | Kunming, Yunnan |
| 28 | 2020 | K326 | WBBSF | Kunming, Yunnan |
| 29 | 2020 | K326 | WBBSF | Kunming, Yunnan |
| 30 | 2020 | K326 | WDB3F | Kunming, Yunnan |
| 31 | 2020 | K326 | WDB3F | Kunming, Yunnan |
| 32 | 2020 | K326 | WDB3F | Kunming, Yunnan |
| 33 | 2020 | K326 | WDX2F | Kunming, Yunnan |
| 34 | 2020 | K326 | WDX2F | Kunming, Yunnan |

Step 2: volatile and semi-volatile components in K326 tobacco leaves before and after mildewing were determined by solid phase microextraction-gas chromatography-mass spectrometry (SPME-GC-MS). The microextraction procedures were as follows:

An extraction head was inserted into a GC injection port and aged at 300° C. for 1 h before starting the experiment until there was no impurity peak. 0.5 G of tobacco leaf sample was weighed into a 22 mL headspace bottle, and 10 µL of naphthalene ethanol solution with a concentration of 100 µg/mL was added as an internal standard for quantification. The extraction flask was placed on a heated stir plate at 80° C. A rubber pad of a bottle cap of a headspace bottle was pierced by using the extraction head of an extraction handle to place the sample in the headspace, then a fiber head in the extraction head was pushed out to adsorb the natural volatile gas of tobacco leaves in the headspace for 50 min. Upon completion of adsorption, the fiber tip was withdrawn and the entire extraction handle was pulled out of the headspace bottle. The extraction head was inserted into the GC injection port of GC-MS, and the fiber head was pushed out to desorb for 2 min at 280° C. to complete the sample injection.

A total of 106 volatile components were detected by GC-MS in the samples, as shown in Table 2.

TABLE 2

List of components in normal tobacco leaves and mildewed tobacco leaves

| Components | Types | |
|---|---|---|
| | Normal tobacco leaves | Mildewed tobacco leaves |
| Olefins | 15 | 16 |
| Alcohols | 6 | 6 |
| Aldehydes | 19 | 16 |
| Ketones | 22 | 20 |
| Heterocycles | 15 | 18 |
| Esters | 12 | 11 |
| Phenols | 3 | 3 |
| Ethers | 1 | 1 |
| Alkanes | 0 | 3 |
| Acids | 0 | 1 |

Figure 3:
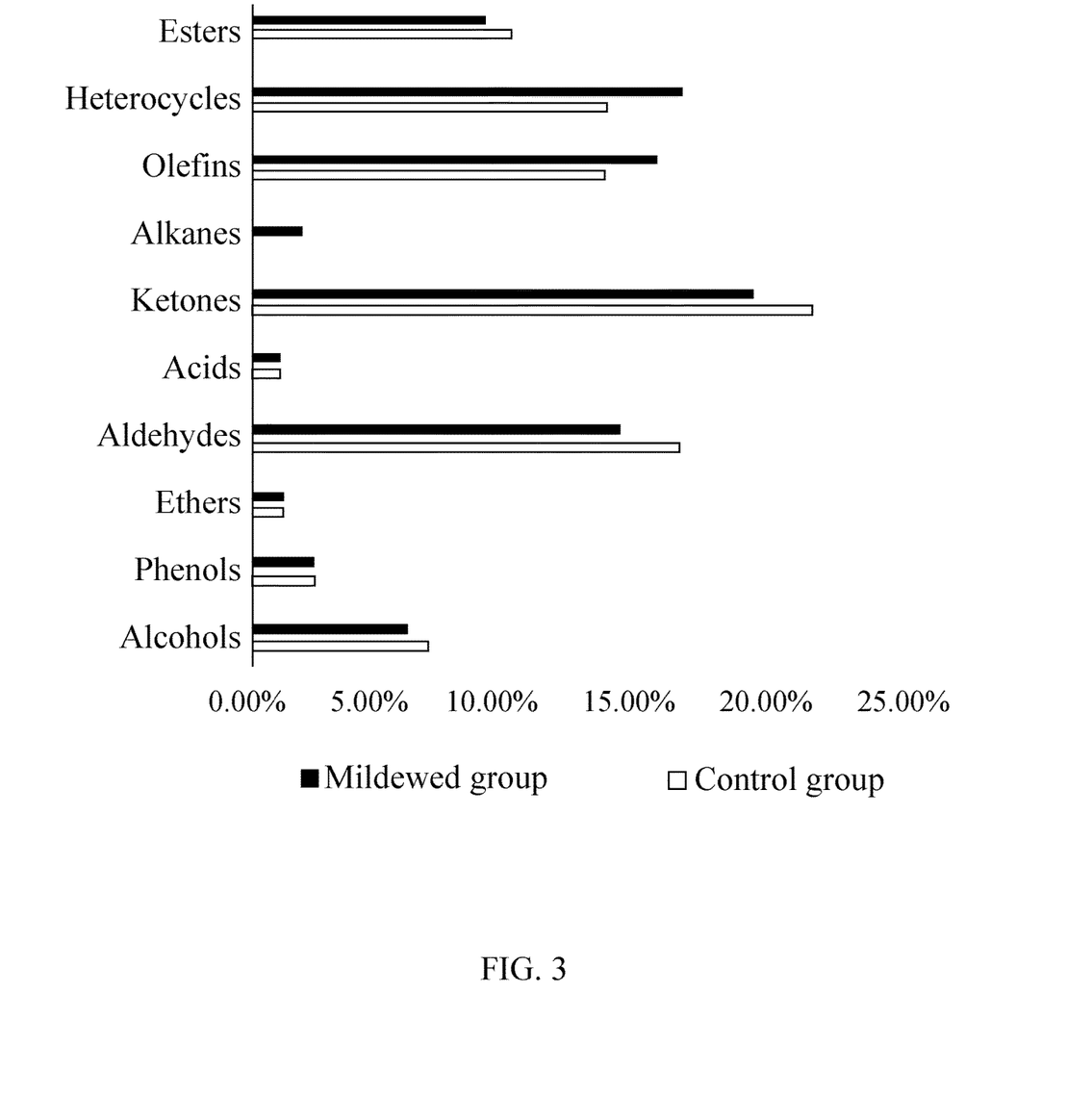
FIG. 3 is a proportion chart of different kinds of compounds provided by an embodiment of the present invention.

Step 3: data retrieval: the mass spectral data were identified by searching the NIST standard library, and the relative content of each substance was calculated by the peak area normalization method. The results of the proportions of different kinds of compounds in the mildewed group and the normal group (control group) are shown in FIG. 3.

Step 4: data processing: the volatile compound quantification results were subjected to data transformation (log 2 Transformation) and normalization (Pareto scaling) processing. The normalization formula is as follows:

$$y = \frac{x_i - x_{min}}{x_{max} - x_{min}} \quad (1)$$

Where $x_i$ is the i-th value in the sample data, $x_{min}$ is the minimum value in the sample data, $x_{max}$ is the maximum value in the sample data, and y is the normalized data of the i-th value.

Step 5: data analysis:

Step (1): volcanic maps were used to analyze volatile compounds in K326 samples before and after mildewing.

A t-test (Student's t-test) was used to analyze the significance of differences, and the volcano map was plotted with log 2 (FC) as the X-axis and −log(p) as the Y-axis.

Volatile compounds of interest in K326 samples before and after mildewing as determined by volcano map analysis are shown in Table 3.

TABLE 3

Volatile compounds of interest in K326 samples before and after mildewing as determined by volcano map analysis

| No. | Compound Name | FC | log2(FC) | p-value | log10(p) |
|---|---|---|---|---|---|
| 70# | 5-methoxy-6,7-dimethyl-benzofuran | 719.9 | 9.492 | 8.57E−17 | 16.067 |
| 60# | 4-vinyl-1,2-dimethoxybenzene | 166 | 7.375 | 5.15E−12 | 11.289 |
| 23# | 1-octen-3-ol | 128.55 | 7.006 | 3.99E−10 | 9.3988 |
| 42# | 1,2-dimethoxy-benzene | 79.059 | 6.305 | 2.44E−07 | 6.6127 |
| 43# | 1,4-dimethoxy-benzene | 60.382 | 5.916 | 0.000693 | 3.1593 |
| 32# | 2,3-cyclopenta [b] pyridine | 60.363 | 5.916 | 6.52E−06 | 5.1859 |
| 34# | 2,4-dimethyl-2,3-heptadien-5-yne | 46.02 | 5.524 | 8.92E−09 | 8.0499 |

TABLE 3-continued

Volatile compounds of interest in K326 samples before and after mildewing as determined by volcano map analysis

| No. | Compound Name | FC | log2(FC) | p-value | log10(p) |
|---|---|---|---|---|---|
| 105# | ethyl oleate | 40.829 | 5.352 | 0.000396 | 3.4023 |
| 53# | 2,4-dichloro-1-methoxy-benzene | 28.167 | 4.816 | 4.13E−16 | 15.385 |
| 30# | 1H-pyrrole-2-carbaldehyde | 3.048 | 1.608 | 0.000392 | 3.407 |
| 36# | Acetophenone | 2.965 | 1.568 | 0.015684 | 1.8046 |
| 92# | methyl hexadecylate | 2.833 | 1.503 | 0.000223 | 3.652 |
| 3# | pyridine | 2.425 | 1.278 | 2.48E−05 | 4.6053 |
| 40# | nonanal | 2.257 | 1.174 | 0.019826 | 1.7028 |
| 94# | cembrene I [3,7,11-trimethyl-1,3,6,10-cyclotetradecaene] | 0.496 | −1.012 | 0.00304 | 2.5171 |
| 82# | megalotrienone IV | 0.484 | −1.048 | 8.45E−07 | 6.0732 |
| 93# | (E,E)-7,11,15-trimethyl-3-methylene-hexadecan-1,6,10,14-tetraene | 0.478 | −1.065 | 5.07E−05 | 4.2946 |
| 98# | methyl heptadecanoate | 0.475 | −1.074 | 0.001263 | 2.8986 |
| 54# | anisole | 0.474 | −1.076 | 0.009727 | 2.012 |
| 10# | Furfural | 0.47 | −1.089 | 0.000301 | 3.5215 |
| 87# | 3,4-dihydro-4,5,6-trimethyl-1 (2H)-naphthalenone | 0.454 | −1.139 | 6.48E−05 | 4.1884 |
| 66# | myosmine [3-(3,4-dihydro-2H-pyrrole-5-yl) pyridine] | 0.451 | −1.147 | 3.57E−06 | 5.4477 |
| 27# | (E,E)-2,4-heptadienal I | 0.419 | −1.255 | 0.000829 | 3.0815 |
| 29# | (E,E)-2,4-heptadienal II | 0.413 | −1.275 | 8.44E−05 | 4.0735 |
| 57# | 2-methoxy-4-vinylphenol | 0.376 | −1.412 | 1.21E−07 | 6.9161 |
| 58# | nicotine | 0.366 | −1.451 | 7.53E−07 | 6.1229 |
| 18# | 5-methyl-2-furanmethanol | 0.354 | −1.497 | 6.77E−07 | 6.1696 |
| 38# | 1-(2-furyl)-2-hydroxyethanone | 0.337 | −1.569 | 0.000618 | 3.2091 |
| 4# | 2-methyl-furan | 0.33 | −1.6 | 3.33E−06 | 5.4772 |
| 73# | 5-hydroxy-3-methyl-1-indanone | 0.326 | −1.617 | 2.54E−08 | 7.5948 |
| 55# | 1-methyl-naphthalene | 0.322 | −1.635 | 0.000431 | 3.3652 |
| 11# | furfuryl alcohol [2-furanmethanol] | 0.321 | −1.639 | 8.72E−07 | 6.0595 |
| 17# | 2-pyridinecarboxaldehyde | 0.317 | −1.656 | 0.000416 | 3.3809 |
| 56# | indole | 0.317 | −1.659 | 0.012122 | 1.9164 |
| 96# | hexadecanoic acid | 0.275 | −1.862 | 3.32E−05 | 4.4783 |
| 88# | tetradecanoic acid | 0.272 | −1.878 | 0.000598 | 3.2235 |
| 75# | 2,3'-bipyridine | 0.271 | −1.882 | 1.31E−08 | 7.8827 |
| 14# | 1-(2-furyl)-ethanone | 0.262 | −1.932 | 1.97E−09 | 8.7051 |
| 95# | cembrene II [3,7,11-trimethyl-1,3,6,10-cyclotetradecaene] | 0.261 | −1.941 | 0.000182 | 3.739 |
| 81# | 3-hydroxy-β-damascone | 0.258 | −1.953 | 1.17E−06 | 5.9329 |
| 83# | 3-oxo-α-ionol | 0.247 | −2.016 | 0.001088 | 2.9633 |
| 102# | dihydrocembrene-3,5-diol II [1,5,9-trimethyl-12-(1-methylethyl)-4,8,13-cyclotetradecatriene-1,3-diol] | 0.236 | −2.085 | 0.023077 | 1.6368 |
| 74# | dihydroactinidiolide | 0.202 | −2.31 | 1.64E−13 | 12.785 |
| 31# | benzyl alcohol | 0.128 | −2.968 | 1.94E−09 | 8.7122 |
| 106# | dihydrocembrene-3,5-diol II [1,5,9-trimethyl-12-(1-methylethyl)-4,8,13-cyclotetradecatriene-1,3-diol] | 0.108 | −3.21 | 0.002959 | 2.5289 |
| 49# | 3-phenyl-furan | 0.07 | −3.827 | 0.069081 | 1.1606 |
| 51# | 5-hydroxymethyl-furfural | 0.061 | −4.045 | 1.52E−06 | 5.8193 |
| 103# | (Z,Z,Z)-9,12,15-octadecatrienoic acid | 0.041 | −4.626 | 0.005018 | 2.2995 |
| 47# | decanal | 0.026 | −5.277 | 0.063313 | 1.1985 |
| 22# | 2,4-dihydroxy-2,5-dimethyl-3 (2H)-furan-3-one | 0.006 | −7.378 | 1.48E−06 | 5.8307 |

It can be seen that the contents of a total of 36 compounds showed a significant decrease, the contents of 14 compounds showed a significant increase, and the contents of the remaining 56 compounds showed no significant change. Among them, the content of the 22 #(2,4-dihydroxy-2,5-dimethyl-3 (2H)-furan-3-one), the 47 #(decanal), the 51 #(5-hydroxymethyl-furfural) and other 36 compounds significantly decreased. The content of the 22 #(2,4-dihydroxy-2,5-dimethyl-3 (2H)-furan-3-one) compound after mildewing was almost 0. The content of 14 compounds such as 70 #(5-methoxy-6,7-dimethyl-benzofuran), the 60 #(4-vinyl-1,2-dimethoxybenzene), and 23 #(1-octen-3-alcohol) increased significantly. The 70 #(5-methoxy-6,7-dimethyl-benzofuran) compound is produced as a new compound by mildew.

Step (2): principal component analysis (PCA) was used to analyze the compound changes of the tobacco leaves before and after mildewing. The PCA procedures were as follows:
(1) Since there are two kinds of tobacco leaves, i.e. mildewed tobacco leaves and normal tobacco leaves, sample n=2; there were 106 kinds of volatile materials, p=106-dimensional random vectors $x=(x_1, X_2, \ldots, x_p)^T$, n samples $x=(x_{i1}, x_{i2}, \ldots, x_{ip})^T$, i=1, 2, ..., n were taken. A sample matrix was constructed, and a normalization transformation was performed on elements in the sample matrix through equation (2):

$$Z_{ij} = \frac{x_{ij} - \bar{x}_i}{s_j}, i = 1, 2, \ldots, n; j = 1, 2, \ldots, p \qquad (2)$$

where $$\bar{x}_i = \frac{\sum_{i=1}^{n} x_{ij}}{n},$$

$$s_j = \sqrt{\frac{\sum_{i=1}^{n}(x_{ij}-\bar{x}_i)}{n-1}},$$

to obtain a normalized matrix Z.

(2) The correlation coefficient matrix R was calculated for the standardized matrix Z.

$$R = [r_{ij}]_p xp = \frac{Z^T Z}{n-1} \quad (3)$$

$$r_{ij} = \frac{\sum z_{kj}^2}{n-1}, i, j = 1, 2, \ldots, p$$

where (3) The characteristic equation $|R-\lambda I_p|=0$ of the correlation coefficient matrix R of the sample was solved to obtain P characteristic roots. When determining a principal component, the value of m was determined according to $$r_{ij} = \frac{\sum_{j=1}^{m} \lambda_j}{\sum_{j=1}^{p} \lambda_j} \geq 0.85,$$

so that the utilization rate of information reached above 85%. For each $\lambda_j$, j=1, 2, . . . , m, equations Rb=$\lambda_j$b were solved to obtain a unit characteristic vector $b_j^o$.

(4) The standardized index variable was converted into the main component.

$$U_{ij}=z_i^T b_j^o, j=1,2,\ldots,m \quad (4)$$

Where $U_{ij}$ is obtained as the main component.

The samples before and after mildewing have a certain degree of discrimination, but cannot be completely separated. The cumulative contribution rate of the first two principal components reaches 76.9% (PC1: 54.6%; PC2: 22.3%).

Step (3): orthogonal projections to latent structures-discrimination analysis (OPLS-DA) was used to further study the difference in chemical components of the tobacco leaves before and after mildewing.

The two main components (the cumulative variance was 38.9%) can be used to distinguish samples of K326 before and after mildewing. When R2X=0.851, and Q2=0.787 show that the model has a suitable explanation and predictability. Specific sources of differences can be obtained from the variable (for classification) importance list (Variable importance for the projection, VIP) of the model. The greater the value of the variable VIP, the greater the effect this variable has on the classification. Compounds with VIP values greater than 1 were selected for the experiment, and VIP values varied from high to low. There were 42 compounds, indicating that these 42 compounds contributed greatly to the determination of whether K326 was mildewed.

Step (4): substances FC≥2 or FC≤0.5 and VIP>1, p<0.05 were selected for visual analysis by Heat map analysis (HMA) and Hierarchical clustering analysis (HCA) to analyze directly the change of volatile compounds in the K326 sample before and after mildew.

The samples before and after mildewing were well clustered and the compounds were divided into two groups.

Step 6: Fisher stepwise discriminant analysis (SDA) was used to establish the identification model of tobacco leaf mildew of K326.

The compounds of FC≥2 or FC≤0.5 and p<0.05, VIP>1 were subjected to Fisher stepwise discriminant analysis to screen out the most effective variables for discriminating mildewed tobacco leaves and establish a discriminant model for discriminating whether K326 tobacco leaves were mildewed.

The results showed that eight compounds, including 18 #(5-methyl-2-furanmethanol), 23 #(1-octen-3-ol), 31 #(benzyl alcohol), 42 #(1, 2-dimethoxy-benzene), 53 #(2, 4-dichloro-1-methoxy-benzene), 70 #(5-methoxy-6, 7-dimethyl-benzofuran), 92 #(methyl hexadecanoate), and 96 #(hexadecanoic acid), were introduced into the discriminant model, and the Fisher linear discriminant functions were established. The discriminant models were as follows:

K326normal tobacco=75.079[18#]−0.892[23#]+
39.071[31#]−7.302[42#]−10.658[53#]−427
[70#]−2.553[92#]+3.175[96#]−6.661.

K326mildewed tobacco=−38.660[18#]+20.989[23#]
4.640[31#]+66.778[42#]+145.421[53#]+12.943
[70#]+5.126[92#]−0.743[96#]−12.170.

In conclusion, in the identification of tobacco leaf mildew of K326 variety, the volatile metabolite components of the mildewed and normal tobacco leaves were analyzed by SPME-GC-MS; the metabolites before and after mildewing were analyzed by PCA and OPLS-DA; through visual and quantitative analysis combined with Fisher SDA, it was found that the discriminant model constructed by 5-methyl-2-furanmethanol, benzyl alcohol, and the other six components could effectively identify normal tobacco and mildewed tobacco leaves. The establishment of this method could provide a reliable strategy for identifying mildewed tobacco and provide a basis for further study on the mechanism of mildew.

It can be seen that the present invention provides a metabonomics-based tobacco leaf mildewing identification method, which determines the volatile and semi-volatile components in tobacco leaves before and after mildewing by using solid phase microextraction-gas chromatography-mass spectrometry, analyzes the differences of metabolites before and after mildewing by using non-targeted metabonomics combined with multivariate statistical analysis and constructs a prediction model to identify the quality of mildewed tobacco leaves, and predicts and monitors mildewed tobacco leaves in advance and in real-time. It can improve the accuracy and efficiency of tobacco mildew identification, improve the quality of cut tobacco, and reduce health hazards to smokers.

The above embodiments illustrated in the figure illustrate the structure, features, and effects of the present invention in detail. The above are only the preferred embodiments of the present invention. However, the present invention does not limit the scope of implementation by the figures. Any changes made according to the concept of the present invention, or equivalent embodiments modified to equivalent changes, still do not exceed the spirit covered by the description and the figures and should be within the scope of protection of the present invention.

The invention claimed is:

1. A metabonomics-based tobacco leaf mildewing identification method, characterized by comprising:
   obtaining tobacco leaves of the same variety, and carrying out artificial mildewing on a certain amount of tobacco leaf samples to obtain normal samples and mildewed samples;
   measuring volatile and semi-volatile components in the tobacco leaves before and after the tobacco leaves are mildewed by adopting a solid phase microextraction-gas chromatography-mass spectrometry method to obtain mass spectrometry data;
   performing data processing on the obtained mass spectrometry data to obtain a proportion content of different types of components in the mildewed samples and the normal samples, and further obtaining a change difference of a content of volatile components in the tobacco leaves before and after mildewing to screen out a discrimination variable of mildewed tobacco leaves; and
   establishing a tobacco leaf mildewing identification model according to the discrimination variable, and performing mildewing identification on the tobacco leaves through the identification model.

2. The metabonomics-based tobacco leaf mildewing identification method of claim 1, characterized in that, performing data processing on the obtained mass spectrometry data, comprising:
   plotting a volcano map by mass spectrometry data, and analyzing the content of volatile components in tobacco leaves before and after mildewing by the volcano map.

3. The metabonomics-based tobacco leaf mildewing identification method of claim 2, characterized in that, performing data processing on the obtained mass spectrometry data, further comprising:
   analyzing changes of volatile components in tobacco leaves before and after mildewing by principal component analysis (PCA).

4. The metabonomics-based tobacco leaf mildewing identification method of claim 3, characterized in that, performing data processing on the obtained mass spectrometry data, further comprising:
   calculating a difference of components in tobacco leaves before and after mildewing by using an orthogonal partial least squares method, to determine a contribution value of various components to tobacco leaf mildewing, and then determining the discrimination variable according to the contribution value.

5. The metabonomics-based tobacco leaf mildewing identification method of claim 4, characterized in that, performing data processing on the obtained mass spectrometry data, further comprising:
   analyzing changes of volatile components in tobacco leaves before and after mildewing directly by visual analysis using thermal map analysis and hierarchical cluster analysis.

6. The metabonomics-based tobacco leaf mildewing identification method of claim 1, characterized in that, obtaining the proportion content of different types of components in the mildewed samples and the normal samples comprises:
   identifying the mass spectrometry data by searching a National Institute of Standards and Technology (NIST) standard spectrum library, and calculating a relative content of each components by peak area normalization method, so as to obtain a proportion result of different components in the mildewed samples and the normal samples; and
   performing data standardization and normalization processing on the obtained proportion result of volatile components to obtain a difference of volatile components content in tobacco leaves before and after mildewing.

7. The metabonomics-based tobacco leaf mildewing identification method of claim 1, characterized in that, carrying out artificial mildewing on a certain amount of tobacco leaves, comprising:
   adjusting a moisture content of the tobacco leaves to make the moisture content of tobacco leaves above 18%, the moisture content of the tobacco leaves being determined by using an oven drying method; and
   placing pretreated tobacco leaves into a constant temperature and humidity box, and adjusting the temperature and relative humidity to be 28° C. and 70%, respectively, to perform a tobacco leaf mildewing test.

8. The metabonomics-based tobacco leaf mildewing identification method of claim 1, characterized in that, a sampling temperature of the tobacco leaves during the microextraction is 280° C. and a desorption lasts for 2 min.

9. The metabonomics-based tobacco leaf mildewing identification method of claim 1, characterized in that, gas chromatography conditions are as follows: injection port temperature: 280° C.; carrier gas: He; flow rate: 1 mL/min; heating conditions: initial temperature: 50° C., holding for 2 min, rising to 140° C. at 5° C./min and holding for 1 min, then rising to 280° C. at 10° C./min and holding for 1 min.

10. The metabonomics-based tobacco leaf mildewing identification method of claim 1, characterized in that, establishing the tobacco leaf mildewing identification model according to the discrimination variable, comprises:
    performing Fisher stepwise discriminant analysis on volatile components in tobacco leaves to screen out the discrimination variable effective for discriminating mildewed tobacco, and establishing a Fisher linear discriminant function according to the discrimination variable.

* * * * *